United States Patent [19]

Ciganek

[11] 4,076,830
[45] Feb. 28, 1978

[54] ALKYLMETHANODIBENZOCYCLOHEPTAPYRROLES

[75] Inventor: Engelbert Ciganek, Kennett Square, Pa.

[73] Assignee: E. I. Du Pont de Nemours and Company, Wilmington, Del.

[21] Appl. No.: 700,964

[22] Filed: Jun. 29, 1976

Related U.S. Application Data

[63] Continuation-in-part of Ser. No. 674,667, Apr. 7, 1976, abandoned, which is a continuation-in-part of Ser. No. 663,430, Mar. 3, 1976, which is a continuation-in-part of Ser. No. 545,001, Jan. 30, 1975, abandoned, which is a continuation-in-part of Ser. No. 448,686, Mar. 6, 1974, abandoned.

[51] Int. Cl.$^2$ .................. C07D 209/70; A61K 31/40
[52] U.S. Cl. .................. 424/274; 260/313.1; 260/326.1; 260/326.5 B; 260/326.62; 260/326.8; 260/570.5 R; 260/570.8 TC
[58] Field of Search .................. 260/326.1, 326.5 B, 260/326.8, 326.62, 313.1; 424/274

[56] References Cited

U.S. PATENT DOCUMENTS

| | | | |
|---|---|---|---|
| 3,123,618 | 3/1964 | Schumann et al. | 260/326.5 B |
| 3,687,936 | 8/1972 | Wilhelm | 260/326.8 |
| 3,726,897 | 4/1973 | Schindler et al. | 260/326.5 B |

FOREIGN PATENT DOCUMENTS

| | | | |
|---|---|---|---|
| 1,336,634 | 11/1973 | United Kingdom | 424/274 |

Primary Examiner—Donald G. Daus
Assistant Examiner—Mary Vaughn
Attorney, Agent, or Firm—Anthony P. Mentis

[57] ABSTRACT

Certain 1-alkyl and 8-alkylmethanodibenzocycloheptapyrroles and their salts are useful as tranquilizers and analgesics. Exemplary are 2-cyclopentylmethyl-1-methyltrans-2,3,8,12b-tetrahydro-1H-3a,8-methanodibenzo[3,4:6,7]cyclohepta[1,2-c]pyrrole hydrochloride of the formula

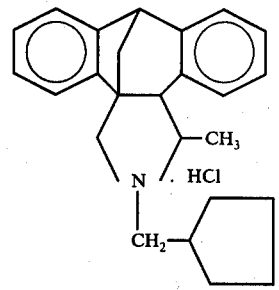

and 2-cyclohexylmethyl-8-methyl-trans-2,3,8,12b-tetrahydro-1H-3a,8-methanodibenzo[3,4:6,7]cyclohepta[1,2-c]pyrrole hydrochloride of the formula

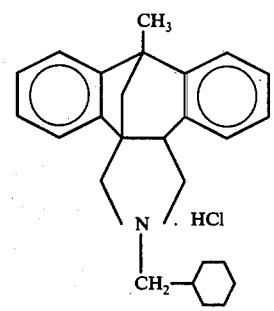

27 Claims, No Drawings

ALKYLMETHANODIBENZOCYCLOHEPTAPYRROLES

RELATED APPLICATIONS

This application is a continuation-in-part of Ser. No. 674,667 filed Apr. 7, 1976 now abandoned, which is a continuation-in-part of Ser. No. 663,430 filed Mar. 3, 1976 which is a continuation-in-part of Ser. No. 545,001, filed Jan. 30, 1975, now abandoned, which in turn is a continuation-in-part of Ser. No. 448,686, filed Mar. 6, 1974, now abandoned.

BACKGROUND OF THE INVENTION

1. Field of the Invention

This invention relates to new polycyclic compounds containing nitrogen, to methods of making the compounds, and to the use of certain of the compounds as tranquilizing agents and as analgesics.

2. Description of the Prior Art

There is no known art describing compounds of the type disclosed in this invention. The closest known art describes the following structures which lack one or more features of the compounds of the invention.

British Patent 1,336,634 (11/7/73)

U.S. 3,687,936 (8/29/72)

U.S. 3,726,897 (4/10/73)

U.S. 3,123,618 (3/3/64)

SUMMARY OF THE INVENTION

This invention is a compound (A) of the formula wherein
- $n$ is zero or 1;
- R is hydrogen, lower alkyl or cycloalkylalkyl of 5–10 carbon atoms, with the proviso that when R is hydrogen $n = $ zero;
- $R^1$ and $R^2$, independently, are hydrogen, lower alkyl, lower alkoxy, nitro, amino, hydroxyl or cyano, with the proviso that at least one of $R^1$ and $R^2$ is hydrogen;
- $R^3$ and $R^4$ individually are H, methyl or ethyl, with with the proviso that only one of $R^3$ and $R^4$ can be H; and (B) a pharmaceutically acceptable acid addition salt of (A) where $n$ is zero.

Preferred are the compounds of structure I where $n$ is zero.

Also preferred are those compounds where $n$ is zero and R is cycloalkylmethyl.

Most preferred for their tranquilizing effect are those compounds where $n$ is zero, R is cycloalkylmethyl, $R^1$ and $R^2$ and $R^3$ are each hydrogen and $R^4$ is methyl.

The compounds where R is other than hydrogen have been found to be tranquilizers for warm-blooded animals and this invention further includes compositions of such compounds with pharmaceutically acceptable inert carriers and to the use of an effective dose of these compounds to tranquilize warm-blooded animals.

The compounds wherein R is H are valuable intermediates for making other members of the class.

The term "lower alkyl" means an alkyl group of 1–4 carbon atoms, including branched alkyl groups.

The term "cycloalkyl group" is employed in the sense of a radical derived from a ring of —$CH_2$— groups by removal of a hydrogen atom.

Compounds of structure I have the trans configuration at the 3a–12b ring fusion with respect to the 12b-hydrogen atom and the 13-methano bridge (or in the alternative, and equivalent thereto, the five-membered nitrogen-containing ring is fused trans to the seven-membered ring). In accordance with usual chemical practice, structure I includes the dl-racemic mixtures as well as the d- and l- optical antipodes of the compounds of the invention.

The compounds of the invention can be made by a rearrangement reaction of bridged ethenoanthracenes.

These latter compounds are made by an internal Diels-Alder reaction of propargyl-substituted 9-anthracene-methylamines, and, in the case of compounds where $R^3 = $ methyl or ethyl and $R^4 = $ hydrogen, alternatively by internal Diels-Alder reaction of propargyl-substituted-9-anthracenemethyleneimines and 9-anthramides as disclosed in the commonly assigned, copending application Ser. No. 511,026, filed Sept. 30, 1974.

In one procedure for the preparation of compounds where $R^4 = H$ a substituted anthracene

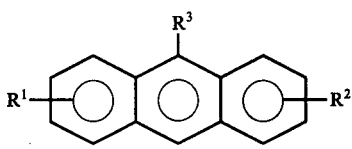

where $R^1$ or $R^2$ can be hydrogen, lower alkyl, lower alkoxy, nitro or cyano groups and $R^3$ is methyl or ethyl, is reacted with oxalyl chloride in the presence of a catalyst to obtain the corresponding 9-anthroyl chloride. The substituted 9-anthroyl chloride is reacted with propargylamine per se or substituted on the nitrogen atom with the aforesaid R groups. These compounds undergo an internal Diels-Alder reaction to give substituted, 9,12-bridged ethenoanthracenes according to the equation.

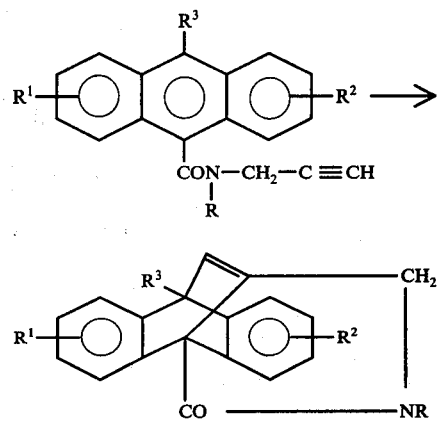

This process can be carried out by heating the alkynylanthramide, either neat or in a suitable inert solvent, preferably an aromatic hydrocarbon, at a temperature of 80° to 250° C for a time sufficient to effect cyclization, generally from 1 to 48 hours depending on the conditions.

Reaction of II with bromine leads to a ring rearrangement reaction to produce products with the skeletal structure of I (stereochemistry unknown) substituted with bromine at the 12b and 13 positions, and containing a 1-carbonyl group. Bromination may be carried out in any inert solvent, preferably a chlorinated aliphatic hydrocarbon with methylene chloride and chloroform being especially preferred. The reaction temperature should be from about $-20°$ C to 100° C, preferably 20°–35° C.

The bromine atoms are readily removed from the intermediate by reductive dehalogenation with a trialkyltin hydride, either neat, or dissolved in an aromatic hydrocarbon solvent. It is preferred to use tributyltin hydride in benzene or toluene. The reaction is carried out at a temperature in the range of 50°–180° C to give compounds having the trans skeletal structure of I which contain a 1-carbonyl group.

Alternatively the bromine atoms can be removed by reaction with zinc and acetic acid at 25° to 120° or with zinc and aqueous dimethylformamide.

The amides containing the 1-carbonyl group are readily converted to the corresponding amines of structure I by reduction of the carbonyl group, preferably with diborane dissolved in an ether solvent such as tetrahydrofuran, at a temperature of 0°–100° C.

Another procedure is to start with an ethenoanthracene of the formula

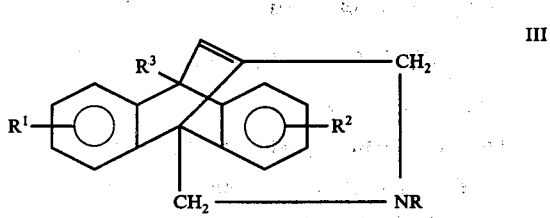

which can be prepared from the corresponding 10-alkyl-9-anthraldehyde or 10-alkyl-9-anthracenemethyl iodide by reaction with propargylamine, followed by internal Diels-Alder reaction, reduction of the carbon-nitrogen double bond (where the starting material is a 10-alkyl-9-anthraldehyde), and alkylation of III(R=H) to obtain the derived N-substituted compound. Alternatively, III(R=H) may be acylated by conventional procedures, and the acyl derivatives may then be reduced with lithium aluminum hydride to obtain the corresponding N-substituted compounds.

In a preferred process for the preparation of III shown in the following equations, the 10-alkyl-9-anthraldehyde compound is reacted with a suitable amine at 25° to 150° in an alcohol solvent to form an imine. The imine is then reduced with a metal hydride reducing agent such as sodium borohydride or sodium cyanoborohydride in an alcohol such as methanol, ethanol, or isopropanol, which can be the same solvent that is employed to form the imine, at a temperature between 0° and 100° C. The resultant secondary amine is then condensed with a propargyl halide, preferably propargyl bromide, in the presence of an inorganic base such as an aqueous solution of an alkali metal carbonate or an organic base which does not react substantially with propargyl bromide, e.g., certain hindered amines including diisopropylethylamine, at a temperature of 0° to 100° C, preferaby at ambient temperatures.

The alkynyl-substituted anthracenes are then cyclized to compounds of Formula III as described hereinabove for the cyclization of the alkynylanthramides.

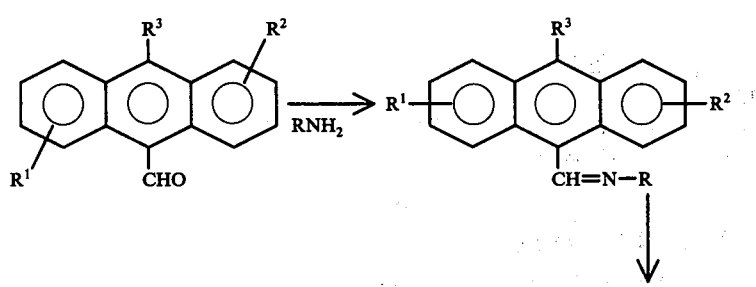

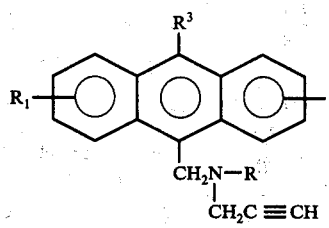 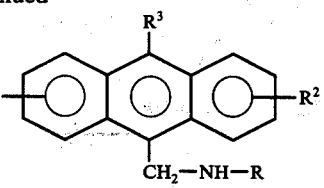

Ring rearrangement of bridged ethenoanthracenes (III) occurs in the presence of strong acids such as p-toluene-sulfonic acid and trifluoroacetic acid at about 70° to 200° C to give products having the skeletal structure of compound I but containing a double bond in the 1-12b position. The rearrangement is preferably carried out with trifluoroacetic acid. This reagent may also be employed for the rearrangement of compounds of structure III wherein R is an acyl group.

The double bond can be reduced to produce the desired trans structure at the 3a-12b carbon atoms by such reagents as sodium cyanoborohydride in acetic acid or by catalytic hydrogenation with a palladium catalyst in acetic acid solvent, or a platinum or rhodium catalyst in tetrahydrofuran. Reduction with a palladium catalyst in tetrahydrofuran gives a mixture of cis and trans racemates. The carbonyl group of the ring rearrangement product of III, R = acyl, must be reduced, e.g., with lithium aluminum hydride, before reduction of the 1-12b double bond to obtain the desired 3a-12b trans products. All of the above reductions are conveniently run at ambient temperatures, but temperatures between 0° C and 60° C are suitable. When catalytic hydrogenation is employed, the pressure of hydrogen should be from about 1 to about 10 atmospheres.

In this method R must be other than H and $R^1$ and $R^2$ can be hydrolytically stable groups. Hydroxyl-substituted compounds of structure I are obtained by cleavage of the corresponding alkoxy compounds, and amino compounds are obtained by reduction of the corresponding nitro compounds. Conventional aromatic nitration reactions of I ($R^1$, $R^2$ = H) can be employed for preparation of nitro derivatives. Additionally, hydroxyl derivatives can be obtained by diazotization of the amino compounds followed by hydrolysis.

Examples of known anthracenes which can be employed as starting materials to produce compounds where $R^4$ is hydrogen include:
  9-methylanthracene
  9-ethylanthracene
  2,9-dimethylanthracene
  1,9-dimethylanthracene
  2,10-dimethylanthracene
  10-ethyl-1-methylanthracene
  1-methoxy-10-methylanthracene
  1,10-dimethylanthracene
  9-methyl-1-anthronitrile
  10-methyl-1-anthronitrile Compounds of structure I wherein R is hydrogen can be alkylated or acylated according to conventional procedures. The acyl derivatives may then be reduced with lithium aluminum hydride to obtain the corresponding N-substituted compounds, for example cycloalkylmethyl groups may be introduced onto the nitrogen atom by acylation with a cycloalkanecarbonyl chloride followed by reduction of the carbonyl group.

A process for the preparation of compounds where $R^4$ is methyl or ethyl and $R^3$ is H, Me or Et is shown in the following equations. α-Methyl-9-anthracenemethylenimine [Martynoff, *Bull. Soc. Chim. France*, 164 (1958)] is reduced with a metal hydride such as sodium cyanoborohydride in an alcohol such as methanol or ethanol, preferably in the presence of an organic acid such as acetic acid, at a temperature between 0° and 100°. The resultant primary amine is then condensed with a propargyl halide, preferably propargyl bromide, in the presence of an inorganic base such as an aqueous solution of an alkali carbonate or hydroxide, or an organic base which does not react substantially with propargyl bromide, e.g., certain hindered amines including diisopropylethylamine, at a temperature of 0°-100°, preferably at ambient temperature. The N-propargylamine so obtained is then cyclized by heating, either neat or in a suitable solvent, preferably an aromatic hydrocarbon, at a temperature of 80°-250° for a time sufficient to effect cyclization. The process scheme may be depicted as follows:

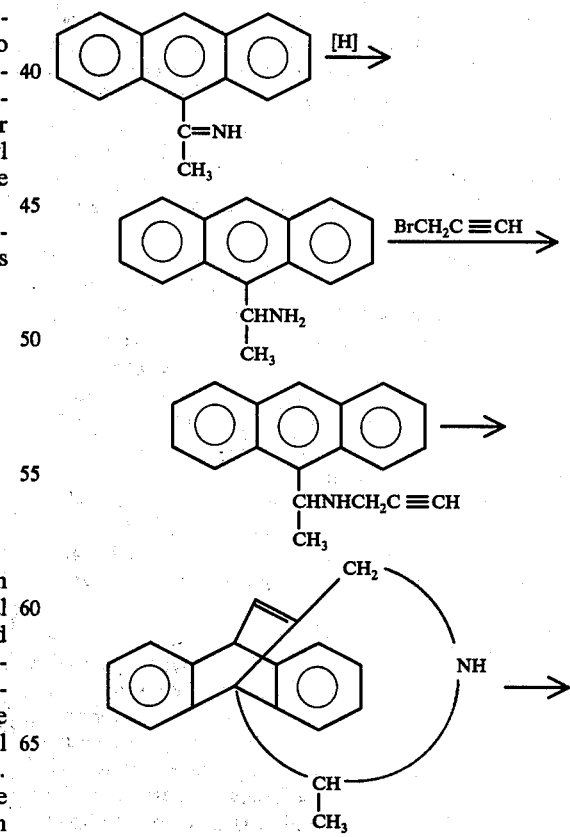

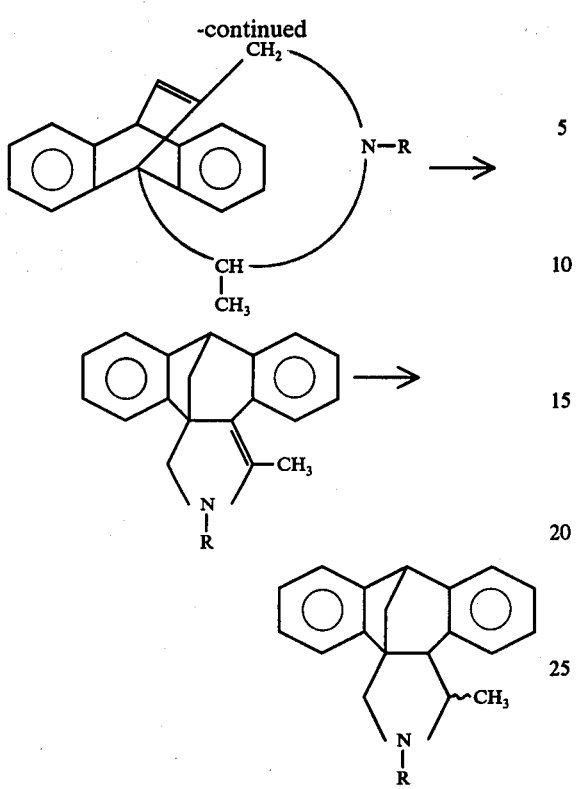

The 1-methyl-1,2,3,5-tetrahydro-5,9b-o-benzenobenz[e]isoindole so obtained is then alkylated or acylated by conventional procedures and the acyl derivatives reduced with lithium aluminum hydride to obtain the corresponding amines. Ring rearrangement of these amines is effected as described for compounds III above. Reduction of the 1-methyl-2,3-dihydro-8H-3a,8-methanodibenzo[3,4:6,7]cyclohepta[1,2-c]pyrroles so obtained may be effected by such reagents as sodium cyanoborohydride in acetic acid or by catalytic hydrogenation with a palladium catalyst in acetic acid solvent. Depending on the methods used, mixtures containing varying amounts of isomers A and B are obtained. Isomers A and B differ in the steric relationship of the 1-methyl group to the 3a,8-methano bridge (either syn or anti).

Use of α-ethyl-9-anthracenemethylenimine as the starting material in the above process leads to compounds where $R^4$ = ethyl. Reaction of 10-methyl or 10-ethyl-9-anthracenecarbonitrile with methylmagnesium iodide gives 10-methyl or 10-ethyl-α-methyl-9-anthracenemethylenimine which, when carried through the above process, gives 8-methyl or 8-ethyl-2-alkyl-1-methyl-2,3,8,12b-tetrahydro-1H-3a,8-methanodibenzo[3,4:6,7]cyclohepta[1,2-c]pyrroles.

In general, the 8, 3a and 12b carbon atoms are asymmetric carbon atoms. Depending on the method of synthesizing the compounds of this invention, there are obtained mixtures of racemates, pure racemates or optical antipodes.

The pharmacologically active compounds of the invention are trans at the 3a–12b ring fusion with respect to the 12b-hydrogen atom and the 13-methano bridge as depicted in structure I. The sterochemistry of the 3a–12b ring fusion was inferred from the crystal structure of the methiodide salt of the compound of structure I, $R^3$=H $R^4$=H, R=CH$_3$, $R^1$=$R^2$=H, prepared by the preferred process of the invention as described above starting with 9-anthraldehyde. Crystals of this compound are monoclinic, space group P2$_1$/c, with cell dimensions of $a$ = 10.219 ± 0.008, $b$ = 14.759 ± 0.026, $c$ = 12.902 ± 0.012A, and $\beta$=100.64 ± 0.06°. The C(1)C(12b)C(3a)C(13) torsion angle is −80.6 ± 1.0° and the HC (12b)C(3a)C(13) torsion angle is 162.2 ± 5.0° where H is the hydrogen on C(12b). The C(1)C(12b)C(3a)C(13) torsion angle is the angle between the C(12b)–C(1) and C(3a)–C(13)bonds in the C(12b)–C(3a) projection (clockwise positive). These data establish that the 3a–12b ring fusion is trans with respect to the 12b-hydrogen atom and the 13-methano bridge.

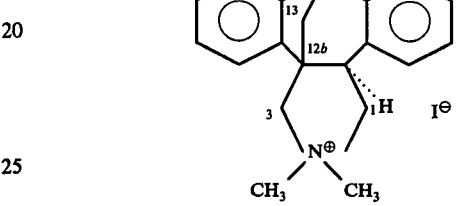

Mixtures of racemates can be separated into the stereoisomeric pure racemates (diasterioisomers) by the use of known physical procedures, e.g., by chromatography or fractional distillation. Pure racemates can be separated into the optical antipodes by conventional methods such as combination with an optically active acid followed by separation by physical means such as recrystallization of the resultant salts.

Reduction with sodium cyanoborohydride, catalytic hydrogenation with Pd in acetic acid, or with Pt or Rh in tetrahydrofuran described above yields the desired trans structure at the ring junction 3a–12b.

The amine compounds of the present invention can be converted to the amine oxides by oxidation of the parent amine with hydrogen peroxide, peracetic acid, perbenzoic acid or the like at ambient temperature or between about 20° C and 60° C.

The amine or amine oxides can be used as such; however, in the case of the amines, addition salts of the active compound with pharmaceutically acceptable acids can be used for administration to warm-blooded animals alone or with an inert carrier. Such salts include hydrochlorides, sulfates, nitrates, phosphates, acetates, tartrates, citrates, lactates, maleates and fumarates of the amine compounds of this invention. The salts can be made, and the free bases can be recovered from the salts, by conventional methods including the use of ion exchange resins, metathetical reactions and the like.

EMBODIMENTS OF THE INVENTION

The following examples are intended to illustrate this invention but should not be construed as fully delineating the scope thereof. All parts and percentages are by weight and all degrees are Celsius unless otherwise stated.

Example 1

2-Cyclohexylmethyl-8-methyl-trans-2,3,8,12b-tetrahydro-1H-3a,8-methanodibenzo[3,4:6,7]cyclohepta[1,2-c]-pyrrole Hydrochloride

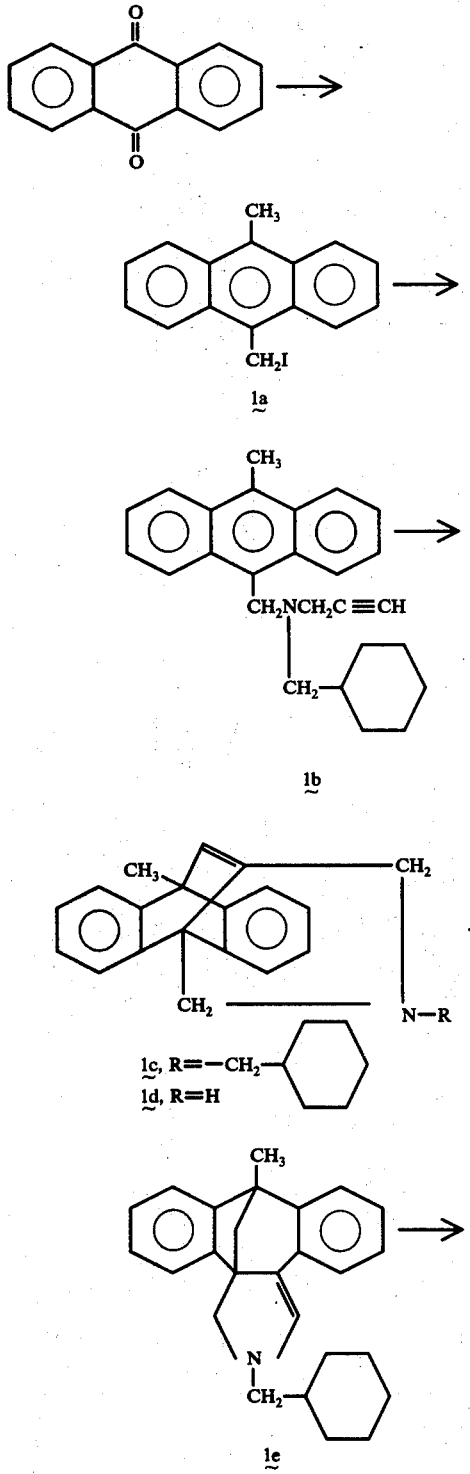

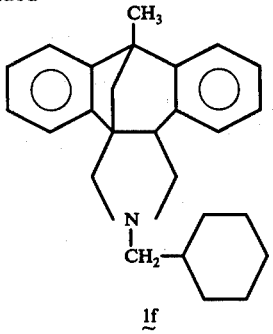

1f

To a stirred solution of 107 ml (0.21 mole) of 2M methyl magnesium iodide in ether in 120 ml of benzene was added 10.0 g (48.0 mmoles) of anthraquinone. The reaction mixture was heated at reflux for 1 hour and then poured slowly onto a mixture of 120 ml of hydriodic acid and 400 ml of methanol with stirring and cooling at $-10°$. This mixture was diluted with 500 ml of acetic acid and cooled to $-20°$. The crystals which separated were collected by filtration and washed with cold water and then with petroleum ether. The 10-methyl-9-anthracenemethyl iodide (1a) weighed 11.0 g, mp. 67°-75° dec.

The product iodide (33.2 mmoles) was added portion wise to a stirred, cooled mixture of 9.3 g (61.6 mmoles) of N-cyclohexylmethylpropargylamine, 50 ml of benzene and 22 ml of ethanol. The reaction mixture was stirred for 1 hr. with cooling and then for several hrs. at room temperature. The volatiles were removed in vacuo and the residue was distributed between methylene chloride and 0.5N sodium hydroxide. The organic layer was separated, washed with water, dried and evaporated to afford 13.4 g of N-cyclohexylmethyl-10-methyl-N-propargyl-9-anthracene-methylamine (1b) as an oil.

Cyclization of 1b was effected by heating it in 50 ml of xylene at reflux temperature overnight. The solution was cooled and the solvent evaporated to leave 22.1 g of crude solid product. Recrystallization from ethanol gave 5.7 g of 2-cyclohexylmethyl-5-methyl-1,2,3,5-tetrahydro-5,9b-o-benzenobenz[e]isoindole(1c), mp. 134°-136°; nmr spectrum: δ 1.0-2.1 (m, 11); 2.1 (s, 3); 2.4 (d, 2); 3.2 (d, 2 Hz, 2); 3.7 (s, 2); 6.1 (t, 2 Hz, 1); 6.8-7.3 (m, 8).

Anal. Calcd. for $C_{26}H_{29}N$: C, 87.89; H, 8.17; N, 3.94 Found: C, 87.98; H, 8.46; N, 4.30 87.86; 8.38; 4.57.

Alternatively, the product 1c was also prepared by heating a mixture of 10-methyl-9-anthraldehyde with propargylamine to give 10-methyl-N-propargyl-9-anthracene-methyleneimine. This product was cyclized by heating it in refluxing xylene, and reduction of the imine double bond gave 5-methyl-1,2,3,5-tetrahydro-5,9b-o-benzenobenz[e]-isoindole (1d). Acylation of 1d with cyclohexanecarbonyl chloride followed by reduction of the carbonyl group with lithium aluminum hydride gave 1c.

A mixture of 3.0 g of 2-cyclohexylmethyl-5-methyl-1,2,3,5-tetrahydro-5,9b-o-benzenobenz[e]isoindole (1c) in excess trifluoroacetic acid was heated in a sealed tube at 175° for 12 hours. The solvent was evaporated, the residue was dissolved in methylene chloride, and the resulting solution was added dropwise to a stirred, cooled mixture of 150 ml of 2N sodium hydroxide and excess methylene chloride. The organic layer was separated, the aqueous layer was extracted with methylene chloride and the combined extracts were washed twice with water and dried. Evaporation of the solvent left 2.6 g of 2-cyclo-hexylmethyl-8-methyl-2,3-dihydro-8H-3a,8-methanodibenzo-[3,4:6,7]cyclohepta[1,2-c]pyrrole (1e) as an oil; nmr spectrum: δ 0.9–2.1 (m, 14); 2.3 (s, 2); 2.8 (t, 2); 3.2 and 3.9 (ABQ, J = 10 Hz, 2); 6.1 (s, 1); 6.7–8.4 (m, 8).

To a cooled solution of 2.6 g of 1e in 25 ml of tetrahydrofuran, dry hydrogen chloride gas was bubbled in for 0.5 min. Then a solution of 1.2 g (19.1 mmoles) of sodium cyanoborohydride in 10 ml of methanol was added immediately and the reaction mixture was stirred at room temperature overnight. The solution was concentrated and the residue was distributed between 1N sodium hydroxide and ether (a small amount of ethanol was added). The organic layer was separated, washed with water, dried and the solvent evaporated to leave 1.85 g of 2-cyclohexylmethyl-8-methyl-trans-2,3,8,12b-tetrahydro-1H-3a,8-methanodibenzo[3,4:6,7]-cyclohepta[1,2-c]pyrrole as an oil; nmr spectrum: δ 0.8–4.0 (m, 23), 6.9–7.5 (m, 7); the former area at 220 MHz resolved from low field to high filed into a doublet (J = 10 Hz, 1); a doublet of doublets (J = 7 and 8 Hz, 1); a doublet of doublets (J = 7 and 10 Hz, 1); a 2 proton multiplet; a 2 proton multiplet; and an ABQ (J = 11 Hz, 2).

The hydrochloride salt was prepared with HCl (g) in ether, mp 280-290° (dec), after crystallization from 2-propanol.

Anal. Calcd. for $C_{26}H_{31}N.HCl$: C, 79.28; H, 8.13; N, 3.56 Found: C, 78.01; H, 8.24; N, 3.71.

EXAMPLE 2

2,8-Dimethyl-trans-2,3,8,12b-tetrahydro-1H-3a,8-methanodibenzo[3,4:6,7]cyclohepta[1,2-c]pyrrole Hydrochloride The title compound was prepared by the process outline for the product of Example 1 using N-methylpropargylamine in place of N-cyclohexylmethylpropargylamine.

10-Methyl-9-anthracenemethyliodide (22.0 g, 66.3 mmoles) and 7.0 g (0.1 mole) of N-methylpropargylamine gave after cyclization, 2,5-dimethyl-1,2,3,5-tetrahydro-5,9b-o-benzenobenz isoindole, mp 151°-2°, after crystallization from 2-propanol; nmr spectrum: δ 2.1 (s, 3); 2.5 (s, 3); 3.2 (d, 2Hz, 2); 3.7 (s, 2); 6.2 (t, 2Hz, 1); 6.8–7.3 (m, 8).

Anal. Calcd for $C_{20}H_{19}N$: C, 87.9; H, 6.96; N, 5.13 Found: C, 87.55; H, 6.95; N, 5.20.

Rearrangement of 2,5-dimethyl-1,2,3,5-tetrahydro-5,9b-o-benzenobenz[e]isoindole in trifluoroacetic acid, as described, gave 2.3 g of 2,8-dimethyl-2,3-dihydro-8H-3a, 8-methanodibenzo[3,4:6,7]cyclohepta[1,2-c]pyrrole; nmr spectrum: δ 1.8 (s, 3); 2.3 (s, 2); 2.8 (s, 3); 3.2 and 3.9 (ABQ, J = 10 Hz, 2); 6.0 (s, 1); 6.8–7.4 (m, 8).

Reduction of 2,8-dimethyl-2,3-dihydro-8H-3a,8-methanodibenzo[3,4:6,7]cyclohepta[1,2-c]pyrrole with sodium cyanoborohydride afforded 1.4 g of 2,8-dimethyl-trans-2,3,8,12b-tetrahydro-1H-3a,8-methanodibenzo[3,4:6,7]cyclohepta[1,2-c]pyrrole as an oil; nmr spectrum (220 MHz): δ 1.75 (s, 1); 2.09 and 2.26 (ABQ, J = 10.5 Hz, 2); 2.5 (s, 3); 2.7 (d, 10.5 Hz, 1); 2.7 (d/d; J = 10.5 and 9 Hz, 1); 3.3 (d/d, J = 10.5 and 7 Hz, 1); 3.4 (d/d, J = 9 and 7 Hz, 1); 3.76 (d, J = 10.5 Hz, 1); 6.9–7.5 (m, 8).

The hydrochloride salt was prepared with HCl (g) in ether, mp 255°-262° (dec), after crystallization from 2-propanol.

Anal. Calcd. for $C_{20}H_{21}N.HCl$: C, 77.05; H, 7.06; N, 4.47; Cl, 11.4 Found: C, 74.66; H, 7.16; N, 4.37; Cl, 11.21.

The following procedure can be employed to produce the homologous 8-ethyl compounds. Condensation of 10-ethyl-9-anthraldehyde (Martin, et al., Bull. soc. chim. Belges 61, 504 (1952)) with, for example, cyclopentylmethylamine would give 10-ethyl-N-cyclopentylmethyl-9-anthracenemethyleneimine. Reduction of the imine with sodium cyanoborohydride would produce 10-ethyl-N-cyclopentylmethyl-9-anthracenemethylamine. Reaction of the amine with propargyl bromide would give the N-propargyl derivative, and cyclization of this product in refluxing xylene in the usual way would produce 2-cyclopentylmethyl-5-ethyl-1,2,3,5-tetrahydro-5,9b-o-benzenobenz[e]isoindole. Rearrangement of this product by heating in trifluoroacetic acid at 175° followed by reduction with sodium cyanoborohydride would produce the desired product, 2-cyclopentylmethyl-8-ethyl-trans-2,3,8,12b-tetrahydro-1H-3a,8-methanodibenzo-[3,4:6,7]cyclohepta[1,2-c]pyrrole.

Other compounds within the scope of this invention which can be made by the procedures described above include compounds of the general formula

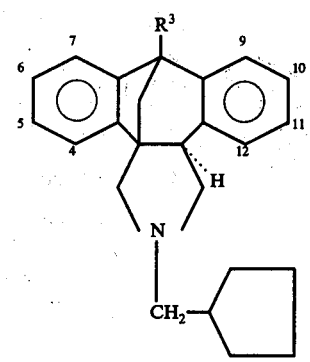

having a single substituent on one of the benzene rings such as the 4-, 5-, 6-, 7-, 9-, 10-, 11- and 12-methyl derivatives, the 4-, 5-, 6-, 7-, 9-, 10-, 11- and 12 t-butyl derivatives, the 4-, 5-, 6-, 7-, 9-, 10-, 11- and 12-nitro derivatives, the 4-, 5-, 6-, 7-, 9-, 10-, 11- and 12-amino derivatives, and the 4-, 5-, 6-, 7-, 9-, 10-, 11- and 12-cyano derivatives. Table I lists various additional compounds which can be made by the procedures described above.

Table I

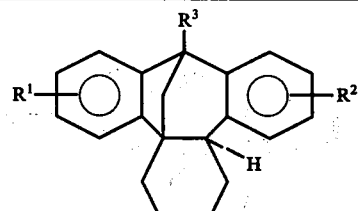

| R | $R^1$ | $R^2$ | $R^3$ |
|---|---|---|---|
| Cyclohexylmethyl | H | H | $C_2H_5$ |
| Cyclopentylmethyl | H | H | $CH_3$ |
| Methyl | H | H | $C_2H_5$ |

Table I-continued

| R | R¹ | R² | R³ |
|---|---|---|---|
| Ethyl | H | H | CH₃ |
| n-Propyl | H | H | CH₃ |
| n-Butyl | H | H | CH₃ |
| i-Butyl | H | H | CH₃ |
| Cyclobutylmethyl | H | H | CH₃ |
| Cycloheptylmethyl | H | H | CH₃ |
| 2-Cyclohexylethyl | H | H | CH₃ |
| 4-Cyclohexylbutyl | H | H | CH₃ |
| Cyclohexylmethyl | CH₃ | H | CH₃ |
| Cyclohexylmethyl | H | t-Butyl | CH₃ |
| Cyclohexylmethyl | CH₃O | H | CH₃ |
| Cyclohexylmethyl | NO₂ | H | CH₃ |
| Cyclohexylmethyl | NH₂ | H | CH₃ |
| Cyclohexylmethyl | OH | H | CH₃ |
| Cyclohexylmethyl | CN | H | CH₃ |

EXAMPLE 3

2-Cyclopentylmethyl-1-methyl-trans-2,3,8,12b-tetrahydro-1H-3a,8-methanodibenzo[3,4:6,7]cyclohepta[1,2-c]pyrrole Hydrochloride.

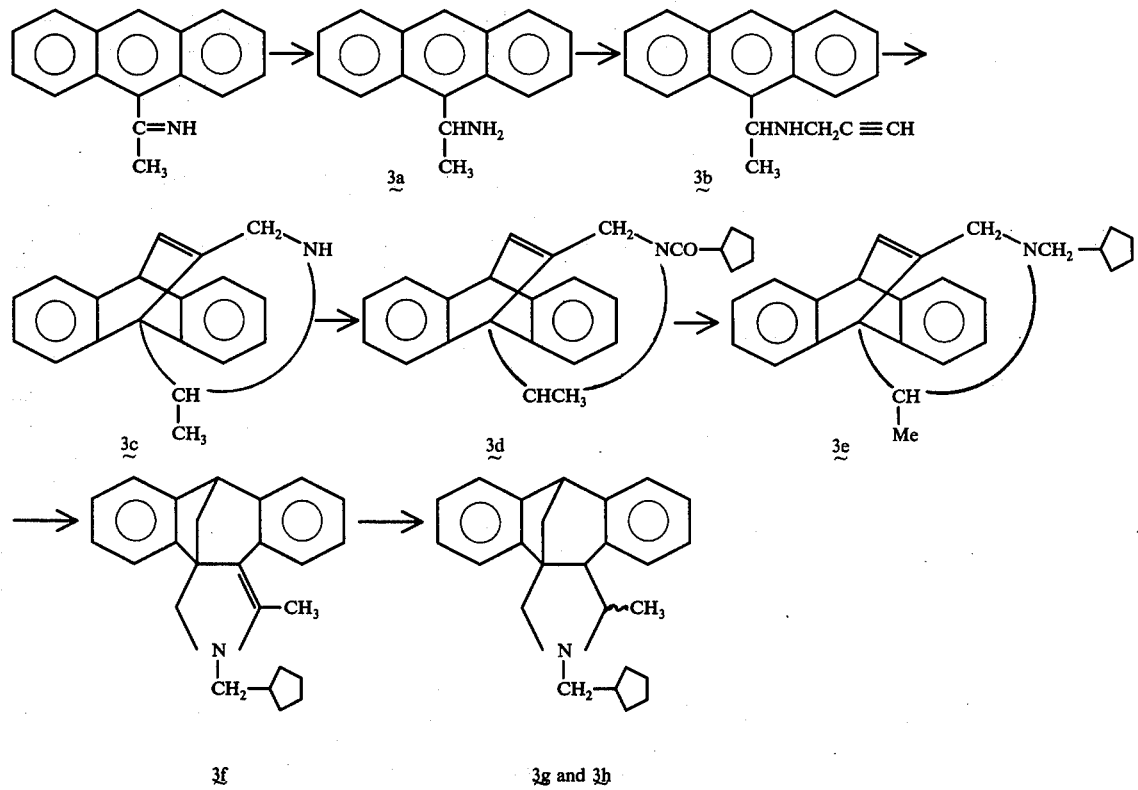

A mixture of 43.6 g of α-methyl-9-anthracenemethylenimine [Martynoff, *Bull. Soc. Chim.* France, 164 (1958)], 200 ml of methanol, 40 ml of acetic acid and 17.2 g of sodium cyanoborohydride was allowed to stand at room temperature for six days. The excess borohydride was destroyed with concentrated hydrochloric acid and the mixture was made basic with aqueous sodium hydroxide solution and extracted with methylene chloride. Removal of the solvent from the dried extract and crystallization of the residue from 100 ml of isopropyl alcohol gave 28.2 g of α-methyl-9-anthracenemethylamine (3a); nmr spectrum: τ 1.2-2.8 (m, 9); 4.4 (q, 7 Hz, 1) 8.1 (s, 2) and 8.3 (d, 7 Hz, 3).

A mixture of 15.5 g of the above amine 3a, 100 ml of 15% aqueous sodium hydroxide solution, 10 ml of propargyl bromide and 100 ml of methylene chloride was stirred at room temperature for 16 hr. The methylene chloride layer was dried and concentrated to give 17.6 g of an oil containing 90% α-methyl-N-propargyl-9-anthracenemethylamine (3b). It was dissolved in 100 ml of toluene and the solution was heated under reflux for 7 hr. Removal of the solvent gave a product containing ca. 80% of 1-methyl-1,2,3,5-tetrahydro-5,9b-o-benzenobenz[e]isoindole (3c). Part of this product (11.5 g) was dissolved in 100 ml of tetrahydrofuran, 10 g of magnesium oxide was added, and the mixture was treated with 10.6 g of cyclopentanecarbonyl chloride. After stirring at room temperature for 20 hr the mixture was filtered and the filtrate was concentrated. The residue was dissolved in methylene chloride and the solution was washed successively with dilute hydrochloric acid, water, and dilute sodium hydroxide solution and dried. The solvent was removed and the residue was crystallized from isopropyl alcohol to give 7.0 g of 2-cyclopentanecarbonyl-1-methyl-1,2,3,5-tetrahydro-5,9b-o-benzenobenz[e]isoindole (3d). Nmr spectrum: τ2.4-3.4 (m, 9); 4.0 (broad, 1); 5.0 (d, 1); 5.3-6.3 (broad, 2) and 6.5-9.1 (m, 12). This product (3d) was reduced by heating with 1.34 g of lithium aluminum hydride in tetrahydrofuran under reflux for 5 hr. The 2-cyclopentylmethyl-1-methyl-1,2,3,5-tetrahydro-5,9b-o-benzenobenz[e]isoindole (3e) so obtained had the followng nmr spectrum: τ 2.2-3.6 (m, 9); 5.0 (d, 1); 6.0-6.7 (m, 2) and 6.8-9.2 (m, 15).

A mixture of 3.6 g of the above product 3e and 20 ml of trifluoroacetic acid, contained in sealed, evacuated Carius tube, was heated to 160° for 8 hr. The excess acid was removed, the residue was dissolved in methylene chloride and the solution was washed with aqueous sodium hydroxide solution. Removal of the solvent gave 3.9 g of 2-cyclopentylmethyl-1-methyl-2,3-dihydro-8H-3a,8-methanodibenzo[3,4:6,7]cyclohepta[1,2-c]pyrrole (3f) still containing some solvent. Nmr spectrum: τ 2.6-3.2 (m, 8 ); 6.0-6.2 (d, 4Hz and d, 10 Hz, 2); 6.6-9.0 (m, 17).

A mixture of 2.1 g of the above product 3f, 20 ml of methanol, 2 ml of acetic acid, and 0.7 g of sodium cyanoborohydride was stirred at room temperature overnight. The excess borohydride was destroyed with concentrated hydrochloric acid, and the mixture was made basic and extracted with methylene chloride. The residue obtained on removal of the solvent was dissolved in ether and treated with hydrogen chloride. The precipitate so obtained was crystallized from isopropyl alcohol to give 0.9 g of 2-cyclopentylmethyl-1-methyl-trans-2,3,8,12b-tetrahydro-1H-3a,8-methanodibenzo[3,4:6,7]-cyclohepta[1,2-c]pyrrole, hydrochloride (3g) being composed of 38% of isomer A and 62% of isomer B. The isomers differ in orientation of the methyl group on C-1 (either syn or anti with respect to the methano bridge).

Catalytic hydrogenation of 1.8 g of 3f with palladium on charcoal in acetic acid, conversion of the product to the hydrochloride and crystallization from isopropyl alcohol gave 0.7 g of 2-cyclopentylmethyl-1-methyl-trans-2,3,8,12b-tetrahydro-1H-3a,8-methanodibenzo[3,4:6,7]-cyclohepta[1,2-c]pyrrole hydrochloride (3h) being composed of 70% of isomer A and 30% of isomer B. Nmr spectrum of isomer A (220 M Hz): τ 2.5-3.2 (m, 8) and 6.0-9.2 (m, 21). The latter region contains among others a doublet (J - 4Hz; H-8) and a doublet at 9.1 (J - 6 Hz, 1-$CH_3$).

Nmr spectrum of isomer B (220 M Hz): τ 2.5-3.2 (m, 8) and 6.0-9.0 (m, 21); the latter region contains a doublet (J - 11 Hz; H-3), a doublet (J - 4 Hz, H-8) and a doublet at 8.6 (J = 6 Hz; 1-$CH_3$).

Compounds of Structure I wherein R is not hydrogen, show activity in the mammalian central nervous system as clinically useful tranquilizers. They can be employed in pharmaceutical compositions composed of the active ingredient, i.e., the compound(s) of the invention, in combination with nontoxic pharmaceutical carriers and additives. In any formulation of the pharmaceutically active agent, the active ingredient will ordinarily be present in an amount from about 0.5% to 95% based on total weight of the composition.

Formulations include injectables and oral dosage forms such as tablets, hard and soft gelatin capsules, suspensions, syrups, elixirs and the like. Additives that can be employed in such formulations include solvents and diluents, lubricants, binding agents, disintegrants, preservatives, colorants, flavors and other additives which are common and well known to the art.

The compounds can be administered as tranquilizing agents by any means that effects contact of the active ingredient compound with the site of action in the body of a warm-blooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipient, the type and severity of illness, kind of concurrent treatment, if any, frequency of treatment and the nature of the effect desired. Generally a daily dosage of active ingredient compound will be from about 0.01 to 200 milligrams per kilogram of body weight. Ordinarily, from 0.05 to 100 and preferably 0.1 to 50 milligrams per kilogram per day in one or more applications per day is effective to obtain the desired results.

The pharmaceutical carrier can be a solid, or a sterile liquid such as water, or an oil, e.g., petroleum oil, animal oil, or vegetable oils such as peanut oil, soybean oil, mineral oil, sesame oil, and the like. In general, water, saline, aqueous dextrose (glucose) and related sugar solutions and glycols such as propylene glycol or polyethylene glycols are preferred liquid carriers, particularly for injectable solutions. Sterile injectable solutions such as saline will ordinarily contain from about 0.5% to 25% and preferably about 1 to 10% by weight of the active ingredient.

Liquid oral administration can be in a suspension, syrup or elixir, in which the active ingredient ordinarily will constitute from about 0.5 to 10% and preferably about 1 to 5% by weight. The pharmaceutical carrier in such composition can be an aqueous vehicle such as an aromatic water, a syrup, a pharmaceutical mucilage, or a hydroalcoholic elixer. Additional information concerning pharmaceutical carriers, diluents and additives can be found in the well-known reference text: Martin, "Remington's Pharmaceutical Sciences."

The general tranquilizer activity of the compounds is evidenced by tests conducted in female white mice in which exploratory loss, ptosis, grip and lift reflexes, catatonia, muscle tone, and pinna twitch reflex are measured. Tests conducted with mice are predictive of human tranquilizer response.

Groups of five Carworth $CF_1S$ female mice, 16-20 g each, were fasted 16-22 hours before use. The mice were put in opaque plastic "shoe-box" cages 15-30 min. before injection, and then treated orally with 4, 12, 36, 108 and 324 mg/kg of the compound to be tested as a 13 mg/ml solution in 1% aqueous distilled water solution of methylcellulose (Methocel ®). Each dose was given in a standard volume of 0.45 ml. Observations were made at 0.5, 2 and 24 hours after dosing. $ED_{50}$ values were calculated for each parameter including death ($LD_{50}$). The $ED_{50}$ and $LD_{50}$ values are the doses at which 50% of the animals would be expected to respond.

Exploratory Activity - The mouse is placed on a stainless steel wire mesh screen (8 inches × 12 inches, 3 mesh per inch, 174 inch mesh openings) "shoe-box" lid (1 inch high) and is observed for normal activities, such as nose movements, head movements with apparent visual examination of the area, and/or walking around on the screen. Absence of or marked depression of these activities for 5 seconds constitutes loss of exploratory activity.

Ptosis - The mouse is picked up by the tail and placed on the screen with its head facing the observer. Bilateral eyelid closure of 50% or more two seconds after placement is considered ptosis.

Catatonia - The mouse is placed with its front paws on the edge of a stainless steel "shoe-box" cover, 1 inch high, covered with adhesive tape. Failure to remove both paws from the cover's edge within 5 seconds constitutes catatonia.

Muscle Tone - The observer gently strokes the abdominal musculature of the mouse with thumb and forefinger. Flaccidity (or rarely, tenseness) is recorded.

Grip and Lift Reflexes - The mouse is gently swung by the tail toward a horizontal 12 gauge wire tautly stretched 25 cm above the bench. After the mouse grasps the wire with its forepaws, its posterior end is held directly below the wire. A normal mouse grasps the wire with its forepaws and immediately lifts its hind limbs to the wire. Failure to grasp the wire with the forepaws in both trials constitutes loss of the grip reflex; failure to lift the hind limbs to grasp the wire with at least one hind paw within 5 seconds constitutes loss of the lift reflex.

The ratio of grip to lift response is significant since the loss of lift reflex is much more pronounced in most compounds exhibiting tranquilizing activity.

Pinna Twitch Reflex - The mouse is placed on the bar 10-20 cm horizontally and 9 cm vertically from a Galton whistle adjusted for 13 kc (5 mm on the whistle scale) and is subjected to several short bursts of sound. If the mouse does not twitch its ears or flatten them against its head the pinna reflex is lost.

With the above-listed responses as criteria, the compounds of the invention exhibit potent tranquilizing activity as shown in Table II below. The $ED_{50}$ values, i.e., the dose which caused the response in 50% of the mice, are tabulated. The results obtained in the tests for two well known commercial tranquilizers, Chlorpromazine and Diazepam, are included for comparison.

Compounds of the Structure I wherein R is not hydrogen, show activity in the mammalian central nervous system as useful analgesics. The analgesic activity of these compounds was evidenced by tests conducted in female white mice in which prevention of the well-known writhing response caused by intraperitoneal injection of phenyl-p-benzoquinone (phenylquinone) was demonstrated. This mouse test is predictive of analgesic response in humans. [E. Siegmund, R. Cadmus and G. Lee, Proc. Soc. Exp. Biol. Med., 95, 729 (1957)].

Groups of five Carworth $CF_1S$ female mice, 18-21 g each, were fasted 17-21 hours and were intubated with analgesic compound as antagonist to phenylquinone at oral doses of 8, 40 and 200 mg/kg or of 0.33, 1, 3, 9, 27 and 81 mg/kg in 0.20 ml 1% methylcellulose (Methocel ®). Thirty minutes later the mice were challenged with phenylquinone, 1.1 mg/kg intraperitoneally (dissolved in pure ethanol and diluted to 5% ethanol with distilled water at 40° C). At 37 minutes to 47 minutes after the administration of the analgesic compound, the mice were observed for appearance of the writhing syndrome. The number of mice which did not writhe at all during the 10 minute observation was recorded as a quantal index of analgesia. $ED_{50}$ values were obtained graphically from the data.

With blockade of phenylquinone-induced writhing as the criterion, the compounds of the invention are analgesic. The $ED_{50}$ values, i.e., the doses which blocked phenylquinone-induced writhing in 50% of the mice, are also tabulated in Table II.

TABLE II

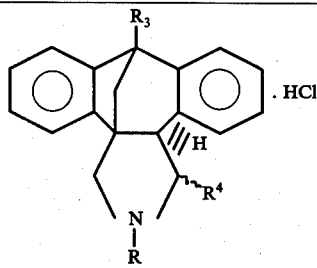

| Active Tranquilizer | | | | $LD_{50}^{(a)}$ | Phenyl-quinone Anal- | Exploratory Loss | | Cata- | Muscle | Reflexes | | | | |
|---|---|---|---|---|---|---|---|---|---|---|---|---|---|---|
| R | $R^3$ | $R^4$ | Ex. | (mg/kg) | gesia | Visual | Ptosis | tonia | Tone | Lift | Grip | Pinna | Tremors | $N^{(b)}$ |
| Cyclohexylmethyl | methyl | H | 1 | >324 | 30 | 87 | 87 | 109 | 109 | 97 | >324 | 109 | >324 | 10 |
| Methyl | methyl | H | 2 | 300 | Active | 60 | 60 | 60 | 36 | 60 | 60 | 60 | 60 | 5 |
| Cyclopentylmethyl | H | methyl | 3g | >324 | Active | 7 | 12 | 20 | 20 | 36 | >324 | 20 | >324 | 5 |
| Cyclopentylmethyl | H | methyl | 3h | >324 | Active | <4 | 20 | 12 | 20 | 20 | >324 | 12 | >324 | 5 |
| Chlorpromazine | | | | 850(c) | — | 7 | 7 | 8 | 8 | 8 | 240 | 5 | >324 | 50 |
| Diazepam | | | | >1000(c) | — | 87 | 79 | 59 | 89 | 4.4 | 78 | 63 | >324 | 50 |

(a)24-hour value
(b)Number of mice
(c)Extrapolated value

I claim;
1. A compound
(A) of the formula

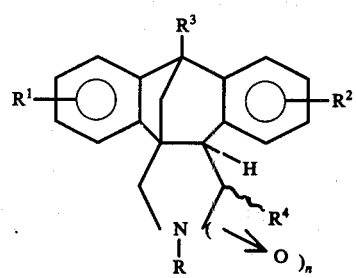

wherein
n is zero or 1;

R is hydrogen, alkyl of 1-4 carbons or cycloalkylalkyl of 5-10 carbon atoms, with the proviso that when R is hydrogen $n$ is zero;

$R^1$ and $R^2$ individually are hydrogen, alkyl or alkoxy each of, 1-4 carbons, nitro, amino, hydroxyl or cyano, with the proviso that at least one of $R^1$ and $R^2$ is hydrogen;

$R^3$ and $R^4$ individually are H, methyl or ethyl, with the proviso that only one of $R^3$ and $R^4$ can be H; and (B) a pharmaceutically acceptable acid addition salt of (A) where $n$ is zero.

2. A compound of claim 1 designated as (A).

3. A compound of claim 1 designated as (B).

4. A compound of claim 1 where $n$ is zero.

5. A compound of claim 1 where $n$ is zero and R is cycloalkylmethyl.

6. A compound of claim 1 where $n$ is zero, R is cycloalkylmethyl, $R^1$, $R^2$ and $R^3$ are each hydrogen and $R^4$ is methyl.

7. A compound in claim 1 where n is zero and R is hydrogen.

8. The compound of claim 1 which is 2-cyclohexylmethyl-8-methyl-trans-2,3,8,12b-tetrahydro-1H-3a,8-methanodibenzo[3,4:6,7]cyclohepta[1,2-c]pyrrole.

9. The hydrochloride of the compound of claim 8.

10. The compound of claim 1 which is 2,8-dimethyl-trans-2,3,8,12b-tetrahydro-1H-3a,8-methanodibenzo-[3,4:6,7]cyclohepta[1,2-c]pyrrole.

11. The hydrochloride of the compound of claim 10.

12. The compound of claim 1 which is 2-cyclopentyl-methyl-1-methyl-trans-2,3,8,12b-tetrahydro-1H-3a,8-methano-dibenzo[3,4:6,7]cyclohepta[1,2-c]pyrrole.

13. The hydrochloride of claim 12.

14. A pharmaceutically active composition comprising an effective tranquillizing amount of a compound of claim 1 where n is zero and R is other than hydrogen and a pharmaceutically acceptable carrier.

15. A pharmaceutically active composition comprising an effective tranquillizing amount of the compound of claim 8 and a pharmaceutically acceptable carrier.

16. A pharmaceutically active composition comprising an effective tranquillizing amount of the compound of claim 9 and a pharmaceutically acceptable carrier.

17. A pharmaceutically active composition comprising an effective tranquillizing amount of the compound of claim 10 and a pharmaceutically acceptable carrier.

18. A pharmaceutically active composition comprising an effective tranquillizing amount of the compound of claim 11 and a pharmaceutically acceptable carrier.

19. A pharmaceutically active composition comprising an effective tranquillizing amount of the compound of claim 12 and a pharmaceutically acceptable carrier.

20. A pharmaceutically active composition comprising an effective tranquillizing amount of the compound of claim 13 and a pharmaceutically acceptable carrier.

21. The method of tranquilizing a warm-blooded animal which comprises administering an effective dose of a composition of claim 14 to said animal.

22. The method of tranquilizing a warm-blooded animal which comprises administering an effective dose of a composition of claim 15 to said animal.

23. The method of tranquilizing a warm-blooded animal which comprises administering an effective dose of a composition of claim 16 to said animal.

24. The method of tranquilizing a warm-blooded animal which comprises administering an effective dose of a composition of claim 17 to said animal.

25. The method of tranquilizing a warm-blooded animal which comprises administering an effective dose of a composition of claim 18 to said animal.

26. The method of tranquilizing a warm-blooded animal which comprises administering an effective dose of a composition of claim 19 to said animal.

27. The method of tranquilizing a warm-blooded animal which comprises administering an effective dose of a composition of claim 20 to said animal.

* * * * *

Page 1 of 3

UNITED STATES PATENT OFFICE
CERTIFICATE OF CORRECTION

PATENT NO. : 4,076,830
DATED : February 28, 1978
INVENTOR(S) : Engelbert Ciganek It is certified that error appears in the above-identified patent and that said Letters Patent are hereby corrected as shown below:

Abstract, line 4, "yltrans" should read -- yl-trans --.

Column 2, line 1, structural formula

" 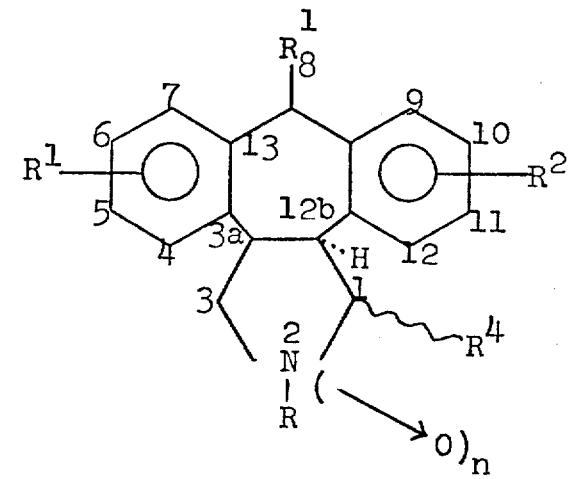 " should read

-- 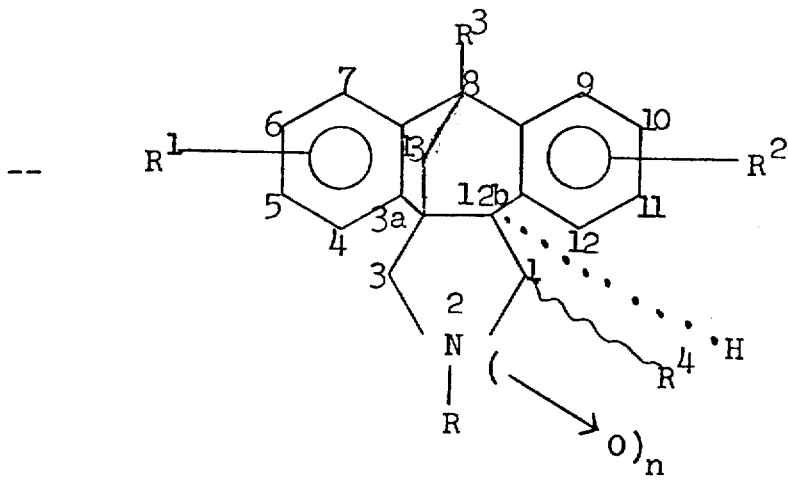 -- .

UNITED STATES PATENT OFFICE
CERTIFICATE OF CORRECTION

PATENT NO. : 4,076,830
DATED : February 28, 1978
INVENTOR(S) : Englebert Ciganek It is certified that error appears in the above-identified patent and that said Letters Patent are hereby corrected as shown below:

Column 3, line 35, "II" should be located adjacent the formula on line 35.

Column 8, line 20, structural formula " 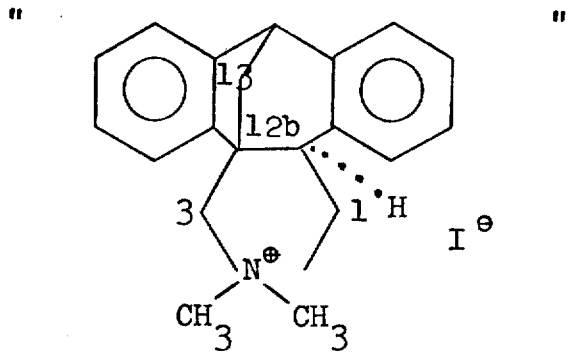 " should read -- 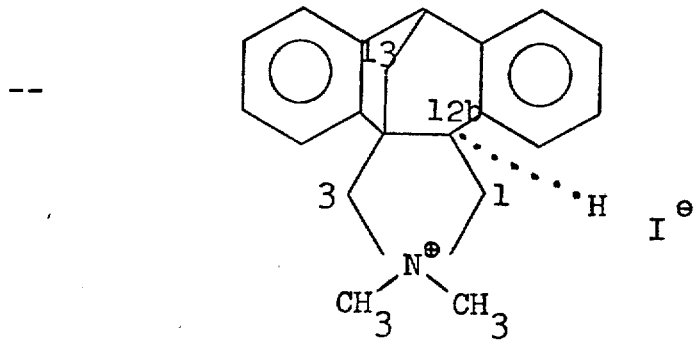 -- .

UNITED STATES PATENT OFFICE
CERTIFICATE OF CORRECTION

PATENT NO. : 4,076,830

DATED : February 28, 1978

INVENTOR(S) : Engelbert Ciganek

It is certified that error appears in the above-identified patent and that said Letters Patent are hereby corrected as shown below:

Column 11, line 40, "outline" should read --outlined--.

Column 11, line 46, "benzenobenz isoindole" should read --benzenobenz[e]isoindole--.

Column 12, line 47, after "tives," insert --the 4-, 5-, 6-, 7-, 9-, 10-, 11-, and 12-hydroxyl derivatives,--.

Column 16, line 53, "174" should read -- 1/4 --.

On the title page add --[*]Notice: The term of this patent subsequent to May 9, 1995 has been disclaimed --

Signed and Sealed this

First Day of August 1978

[SEAL]

Attest:

RUTH C. MASON
Attesting Officer

DONALD W. BANNER
Commissioner of Patents and Trademarks